(12) United States Patent
Tan et al.

(10) Patent No.: US 10,470,742 B2
(45) Date of Patent: Nov. 12, 2019

(54) SYSTEMS AND METHODS FOR SPECKLE REDUCTION

(71) Applicant: Covidien LP, Mansfield, MA (US)

(72) Inventors: Wei Tan, Shanghai (CN); Ravi Durvasula, Cheshire, CT (US)

(73) Assignee: Covidien LP, Mansfield, MA (US)

(*) Notice: Subject to any disclaimer, the term of this patent is extended or adjusted under 35 U.S.C. 154(b) by 440 days.

(21) Appl. No.: 14/561,416

(22) Filed: Dec. 5, 2014

(65) Prior Publication Data

US 2015/0305715 A1 Oct. 29, 2015

Related U.S. Application Data

(60) Provisional application No. 61/985,116, filed on Apr. 28, 2014.

(51) Int. Cl.
*A61B 8/00* (2006.01)
*A61B 8/12* (2006.01)
(Continued)

(52) U.S. Cl.
CPC ............ *A61B 8/4494* (2013.01); *A61B 8/085* (2013.01); *A61B 8/12* (2013.01); *A61B 8/15* (2013.01); *A61B 8/403* (2013.01); *A61B 8/445* (2013.01); *A61B 8/5207* (2013.01); *A61B 8/5269* (2013.01); *A61B 17/29* (2013.01); *G01S 7/52077* (2013.01); *G01S 15/8913* (2013.01); *G01S 15/8915* (2013.01);
(Continued)

(58) Field of Classification Search
CPC ......... A61B 8/00; A61B 8/0875; A61B 8/145; A61B 8/4281; A61B 8/4461; A61B 8/4466; A61B 8/4494; A61B 8/461; A61B 8/483; A61B 8/523
See application file for complete search history.

(56) References Cited

U.S. PATENT DOCUMENTS 5,474,072 A 12/1995 Shmulewitz
5,479,927 A 1/1996 Shmulewitz
(Continued)

FOREIGN PATENT DOCUMENTS

CN 102670256 A 9/2012
EP 2 325 672 5/2011
(Continued)

OTHER PUBLICATIONS

European Search Report dated Sep. 29, 2015, issued in European Application No. 14199785.

*Primary Examiner* — Joel Lamprecht (57) ABSTRACT

Ultrasound imaging systems and methods are disclosed to reduce speckle. The systems and methods include the use of an ultrasound device and a controller. The ultrasound device includes an end effector having a first jaw member and a second jaw member opposite the first jaw member. The first jaw member and the second jaw member move relative to one another to grasp tissue therebetween. A first ultrasound transducer is disposed on the first jaw member and a second ultrasound transducer is disposed on the second jaw member. The controller receives a first signal from the first ultrasound transducer and a second signal from the second ultrasound transducer and generates an image based on the first signal and the second signal.

19 Claims, 4 Drawing Sheets

(51) Int. Cl.
  *A61B 8/08* (2006.01)
  *A61B 8/15* (2006.01)
  *G01S 7/52* (2006.01)
  *G01S 15/89* (2006.01)
  *A61B 17/29* (2006.01)
  *A61B 90/00* (2016.01)

(52) U.S. Cl.
  CPC ...... *G01S 15/8929* (2013.01); *G01S 15/8995* (2013.01); *A61B 8/5253* (2013.01); *A61B 2090/3784* (2016.02)

(56) References Cited

U.S. PATENT DOCUMENTS

| | | |
|---|---|---|
| 5,653,235 A | 8/1997 | Teo |
| 5,664,573 A | 9/1997 | Shmulewitz |
| 5,938,613 A | 8/1999 | Shmulewitz |
| 6,524,247 B2 | 2/2003 | Zhao et al. |
| 6,911,008 B2 | 6/2005 | Pelissier et al. |
| 2002/0173719 A1 | 11/2002 | Zhao et al. |
| 2004/0162596 A1 | 8/2004 | Altshuler et al. |
| 2007/0004984 A1* | 1/2007 | Crum et al. ............. A61B 8/06 600/471 |
| 2009/0177085 A1 | 7/2009 | Maxwell et al. |
| 2009/0287223 A1* | 11/2009 | Pua ..................... A61B 8/0833 606/130 |
| 2011/0118605 A1 | 5/2011 | Kim |
| 2013/0243296 A1 | 9/2013 | Nandi et al. |
| 2014/0066759 A1 | 3/2014 | Healey |
| 2014/0100459 A1 | 4/2014 | Xu et al. |

FOREIGN PATENT DOCUMENTS

| | | |
|---|---|---|
| EP | 2684525 A1 | 1/2014 |
| JP | 2003111763 A | 4/2003 |
| WO | 2008146198 A2 | 12/2008 |
| WO | 2009020617 A1 | 2/2009 |
| WO | 2010082146 A1 | 7/2010 |
| WO | 2013188625 A1 | 12/2013 |

* cited by examiner

SYSTEMS AND METHODS FOR SPECKLE REDUCTION

CROSS-REFERENCE TO RELATED APPLICATIONS

This application claims the benefit of and priority to U.S. Provisional Patent Application No. 61/985,116, filed Apr. 28, 2014, the entire disclosure of which is incorporated by reference herein.

BACKGROUND

1. Technical Field

The present disclosure generally relates to ultrasound imaging systems and methods. Particularly, the present disclosure relates to speckle reduction in ultrasound images.

2. Description of Related Art

Today, many surgical procedures are performed through small openings in the skin, as compared to the larger openings typically required in traditional procedures, in an effort to reduce both trauma to the patient and recovery time. Such procedures are known as "minimally invasive" procedures. During the course of minimally invasive procedures, the nature of the relatively small opening through which surgical instruments are manipulated, and/or the presence of sub-surface tissue structures, may obscure a direct line-of-sight to the target surgical site. Accordingly, it would be desirable to provide a method of sub-surface visualization that is not limited by the geometry of the minimally invasive surgical site.

One such technique involves the use of ultrasound to provide clinicians with the ability to image sub-surface tissue structures. Ultrasound imaging relies on different acoustic impedances of adjacent tissue structures to provide the contrast used for imaging and identifying separate tissue structures. Ultrasound imaging possesses several advantages that are attractive for real-time application in surgical procedures, e.g., minimal associated radiation and relatively small and inexpensive imaging hardware.

One type of ultrasound imaging technique is a B-mode, which obtains a two-dimensional cross-section of the tissue being imaged. The B-mode ultrasound technique always generates random speckle noise in the image. Speckle is a random, deterministic interference pattern in an image formed with coherent radiation of a medium containing many sub-resolution scatters. The texture of the observable speckle pattern does not correspond to underlying structures. To reduce the noise, a technique called compound imaging steers acoustic energy at different angles and averages the values of the pixels at each location obtained using acoustic signals from different angles.

Due to limitations in a traditional linear array, the acoustic energy is generally steered less than 20°. Because there is a lot of overlap even after the beams are steered, there is a strong correlation between signals from steered beams. The speckle pattern generated by these beams is therefore highly correlated thereby limiting the effect of the compounding technique.

SUMMARY

In an aspect of the present disclosure, an ultrasound imaging system is provided that reduces speckle in an ultrasound image. The system may include an ultrasound device that has an end effector with a first jaw member and a second jaw member opposite the first jaw member. The first jaw member and the second jaw member move relative to one another to grasp tissue therebetween. A first ultrasound transducer is disposed on the first jaw member and a second ultrasound transducer is disposed on the second jaw member. The system also includes a controller configured to receive a first signal from the first ultrasound transducer and a second signal from the second ultrasound transducer. The controller generates an image based on the first signal and the second signal.

Each of the first and second ultrasound transducers may include a linear array of ultrasound transducers.

In some aspects, the first ultrasound transducer may emit acoustic energy and receive reflected energy. The first ultrasound transducer may convert the reflected energy into the first signal. The second ultrasound transducer may emit acoustic energy and receive reflected energy. The second ultrasound transducer may convert the reflected energy into the second signal.

In other aspects, the second ultrasound transducer emits acoustic energy and the first ultrasound transducer receives reflected energy based on the acoustic energy from the second ultrasound transducer. The first ultrasound transducer converts the reflected energy into the first signal. The first ultrasound transducer emits acoustic energy and the second ultrasound transducer receives reflected energy based on the acoustic energy from the first ultrasound transducer. The second ultrasound transducer converts the reflected energy into the second signal.

The controller may convert the first signal into a first A-line and the second signal into a second A-line. The first A-line and the second A-line may be averaged to produce a third A-line. The controller may generate the image from the third A-line.

In other aspects of the present disclosure, methods for reducing speckle in an ultrasound image provided by an ultrasound imaging system are disclosed. The ultrasound imaging system has a controller and an ultrasound device that includes an end effector having a first ultrasound transducer opposite a second ultrasound transducer. One such method includes emitting a first acoustic energy from the first ultrasound transducer and emitting a second acoustic energy from the second ultrasound transducer. A first reflected energy based on the first acoustic energy is received at the first ultrasound transducer and a second reflected energy based on the second acoustic energy is received at the second ultrasound transducer. An image is generated based on the first reflected energy and the second reflected energy.

Another method includes emitting a first acoustic energy from the first ultrasound transducer and emitting a second acoustic energy from the second ultrasound transducer. A first reflected energy based on the second acoustic energy is received at the first ultrasound transducer and a second reflected energy based on the first acoustic energy is received at the second ultrasound transducer. An image is generated based on the first reflected energy and the second reflected energy.

The above methods may also include converting the first reflected energy into a first signal that is provided to the controller and converting the second reflected energy into a second signal that is provided to the controller.

In the above methods, the first signal may be converted into a first A-line and the second signal may be converted into a second A-line. The first A-line and the second A-line may be averaged to generate the third A-line and an image may be generated based on the third A-line.

BRIEF DESCRIPTION OF THE DRAWINGS

Embodiments of the present disclosure will be readily appreciated by reference to the drawings wherein.

DETAILED DESCRIPTION

Particular embodiments of the present disclosure are described hereinbelow with reference to the accompanying drawings; however, it is to be understood that the disclosed embodiments are merely examples of the disclosure and may be embodied in various forms. Well known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures. The term "clinician" refers to any medical professional (i.e., doctor, surgeon, nurse, or the like) performing a medical procedure involving the use of embodiments described herein. As shown in the drawings and described throughout the following description, as is traditional when referring to relative positioning on a surgical instrument, the term "proximal" or "trailing" refers to the end of the apparatus which is closer to the clinician and the term "distal" or "leading" refers to the end of the apparatus which is farther away from the clinician.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, or the like. The controller may also include a memory to store data and/or algorithms to perform a series of instructions.

Any of the herein described methods, programs, algorithms or codes may be converted to, or expressed in, a programming language or computer program. A "Programming Language" and "Computer Program" is any language used to specify instructions to a computing device, and includes (but is not limited to) these languages and their derivatives: Assembler, Basic, Batch files, BCPL, C, C+, C++, Delphi, Fortran, Java, JavaScript, Machine code, operating system command languages, Pascal, Perl, PL1, scripting languages, Visual Basic, metalanguages which themselves specify programs, and all first, second, third, fourth, and fifth generation computer languages. Also included are database and other data schemas, and any other metalanguages. For the purposes of this definition, no distinction is made between languages which are interpreted, compiled, or use both compiled and interpreted approaches. For the purposes of this definition, no distinction is made between compiled and source versions of a program. Thus, reference to a program, where the programming language could exist in more than one state (such as source, compiled, object, or linked) is a reference to any and all such states. The definition also encompasses the actual instructions and the intent of those instructions.

Any of the herein described methods, programs, algorithms or codes may be contained on one or more machine-readable media or memory. The term "memory" may include a mechanism that provides (e.g., stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

The present disclosure is directed to systems and methods for reducing speckle in an ultrasound image. The systems and methods utilize an ultrasound device that has an end effector with opposing jaw members that are configured to grasp tissue. Each of the jaw members includes a linear array of transducers that emit acoustic energy and receive reflected energy. The reflected energy is converted into first and second A-lines by a controller. The controller then averages the first and second A-lines to generate a third A-line which is used to generate an image. The systems and method described herein transmit and receive acoustic energy from opposite sides of the jaw members in order to provide redundancy that enables image compounding. Because the acoustic energy is transmitted or emitted from opposite directions, the correlation of speckles are much smaller than conventional beam-steering techniques. Thus, averaging the A-lines with opposite compounding may achieve better speckle reduction.

Referring initially to FIGS. 1-3B, an ultrasound system 100 includes an ultrasound device 102. The ultrasound device 102, as shown may also be coupled with an ultrasound generator 103, a controller 104, and a display 106. The ultrasound device 102, as shown, includes a handle assembly 108, an elongate shaft member 110 extending therefrom and defining a longitudinal axis "X", and an end effector 112 coupled to a distal portion of the elongate shaft member 110.

The handle assembly 108 generally includes a housing 114, a stationary handle 116, and a movable handle 118 configured to approximate toward the stationary handle 116 to activate the ultrasound device 102 and cause movement of the end effector 112. A trigger 120 may also cause movement of the end effector 112, as will be described further below. A more detailed description of the features and function of handle assembly 108 and subsequent actuation thereof are disclosed in U.S. Pat. No. 5,865,361 to Milliman et al., the entire contents of which are incorporated herein by reference.

Figure 2A:
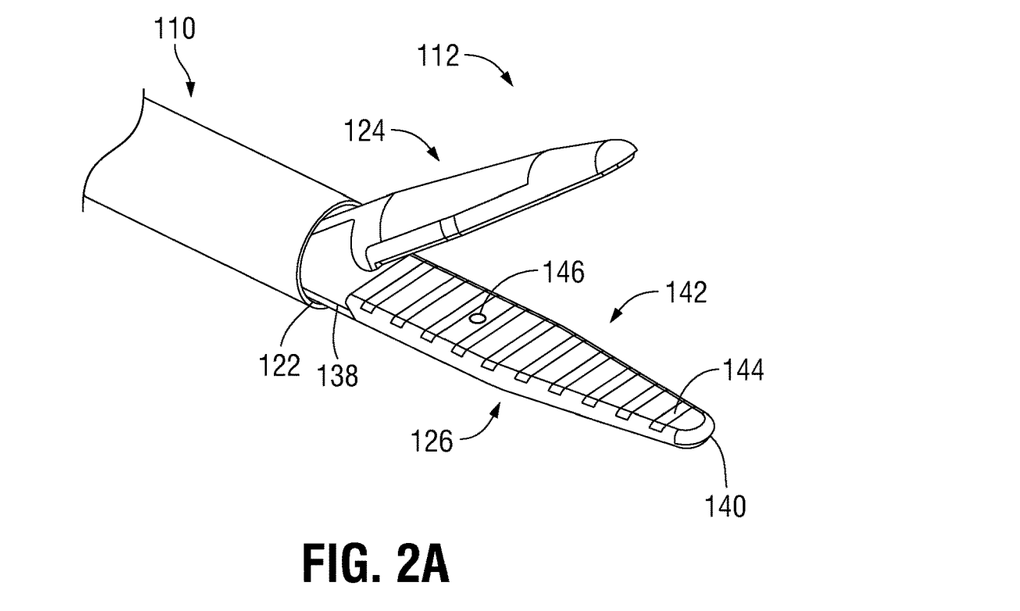
FIG. 2A is a perspective view of the end effector portion of the ultrasound device.
Figure 2B:
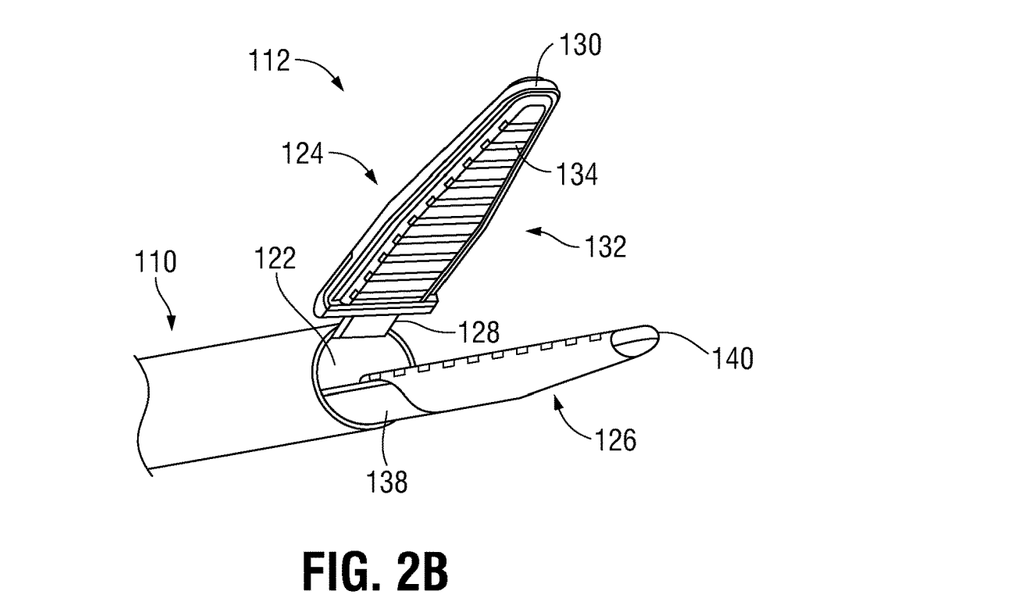
FIG. 2B is another perspective view of the end effector portion of the ultrasound device.

The elongate shaft member 110, as shown, is a substantially straight, tubular member defining a channel 122 therethrough (FIG. 2A). The channel 122 is configured to receive a portion of the end effector 112, as will be described further below. The elongate shaft member 110 may be coupled to the handle assembly 108 in any suitable manner, e.g., adhesion or welding, snap fit, interference fit, or press fit.

The end effector 112, as shown, includes a first jaw member 124 and a second jaw member 126. The first jaw member 124 is pivotably attached to a distal portion of the elongate shaft member 110. Accordingly, the first jaw member 124 is configured to approximate, i.e., pivot radially toward, the second jaw member 126 to capture tissue therebetween (as shown in FIG. 3B), as will be described further below. Additionally, the second jaw member 126 may be configured to axially translate with respect to the elongate shaft member 110 to reconfigure the relative positioning of the first jaw member 124 and the second jaw member 126, as will be described further below. The first jaw member 124 and the second jaw member 126 are configured to move independently of each other.

Figure 1:
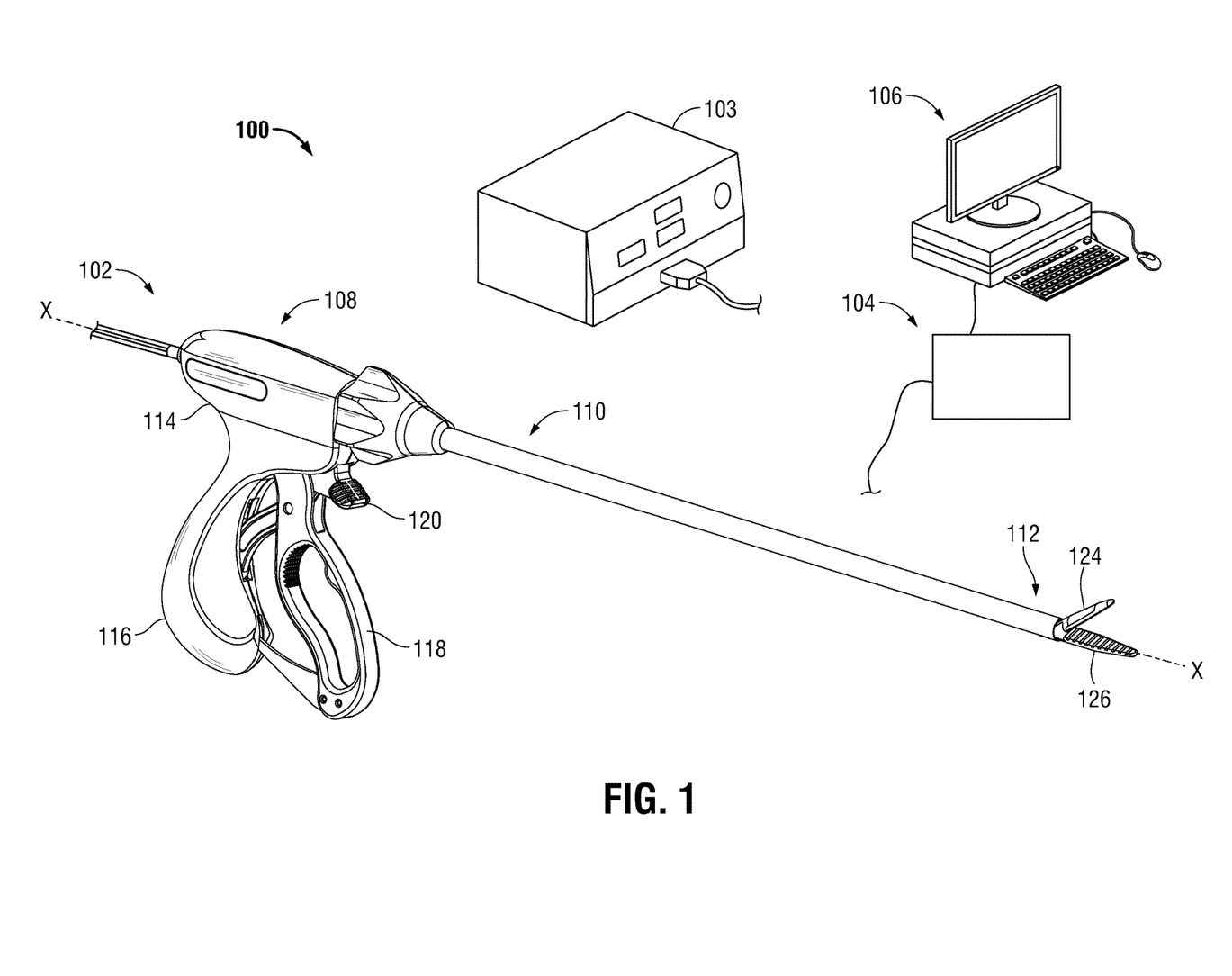
FIG. 1 is a perspective view of an ultrasound imaging system including an ultrasound device according to the present disclosure.

The first jaw member 124 is pivotably connected to the elongate shaft member 110 via a hinge 128. The hinge 128 may include a pivot point on one or more of the elongate shaft member 110 and the first jaw member 124, and is configured to approximate toward the second jaw member 126 upon actuation of the handle assembly 108 (FIG. 1). The first jaw member 124 may be actuated by the handle assembly 108, and is acted upon by the action of, e.g., a drive member, drive cable, or dynamic clamping member. In embodiments, the hinge 128 may be configured as a leaf spring to bias the first jaw member 124 towards a resting, unapproximated position.

The first jaw member 124, as shown, may have a tapered profile along the longitudinal axis X (FIG. 1) to define a distal surface 130 that is configured to make an initial contact with a tissue surface, e.g., to push, move, or dilate tissue. The first jaw member 124 also defines a tissue contacting surface 132. The tissue contacting surface 132, as shown, may have a substantially flat profile, and may including a plurality of ultrasound transducers 134 thereon. The ultrasound transducers 134 may be arranged in longitudinally spaced rows, as shown, or may have any other desirable arrangement on the tissue contacting surface 132 of the first jaw member 124.

The ultrasound transducers 134 may be any type of transducer or sensor that is configured to detect the presence and/or properties, e.g., amplitude and/or wavelength, of ultrasonic energy. Accordingly, the ultrasound transducers 134 are configured to convert energy reflected off tissue structures having different acoustic impedances into distinct electrical signals, as will be described further below. In embodiments, the ultrasound transducers 134 may be configured to generate and/or transmit ultrasonic energy as well as to receive energy.

Figure 3A:
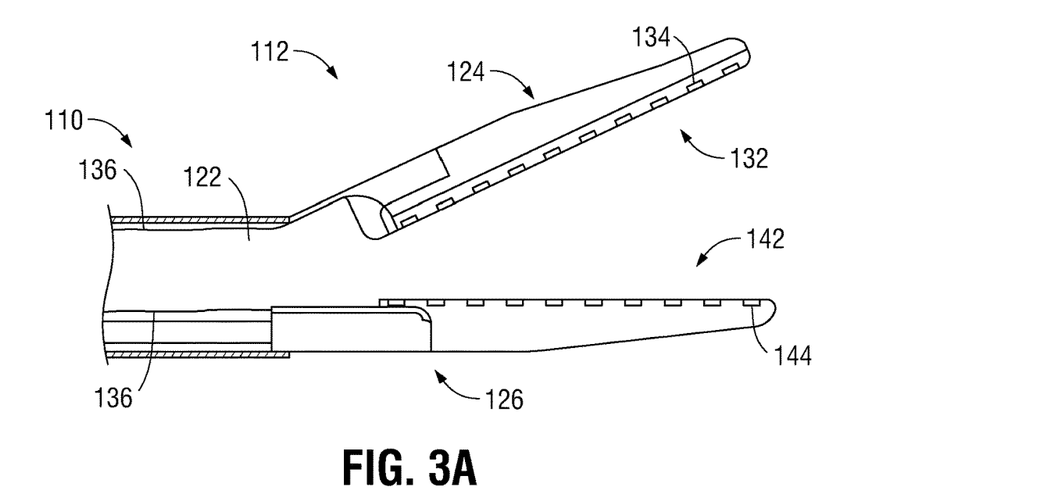
FIG. 3A is a side view, shown partially in cutaway, of the end effector portion of the ultrasound device.
Figure 3B:
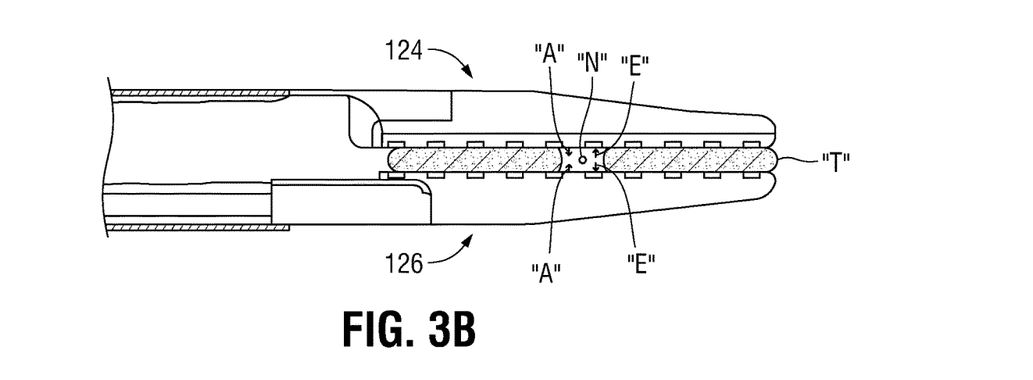
FIG. 3B is a side view of the end effector portion of the ultrasound device.

Accordingly, the ultrasound transducers 134 may be electrically coupled to a power source through electrical wires 136 (FIG. 3A). The electrical wires 136 may be any type of cable or conduit suitable for transmitting electrical energy between the ultrasound transducers 134 and a source of electrical energy, e.g., a battery, generator, or local power grid (not shown). The electrical wires 136 may also electrically couple the ultrasound transducers 134 with the ultrasound generator 103, the controller 104, and/or the display 106 (FIG. 1).

The second jaw member 126, as shown, may be aligned radially within the interior wall of the elongate shaft member 110 that defines the channel 122. Accordingly, the second jaw member 126 may be disposed such that the second jaw member 126 is aligned for passage into the channel 122. The second jaw member 126 is supported on a drive member 138 that extends proximally through the channel 122 of the elongate shaft member 110, and is operably coupled with trigger 120 of the handle assembly 108 (FIG. 1). Drive member 138 is operably coupled with the trigger 120 of the handle assembly 108 such that actuation of the trigger 120 causes retraction or extension of the drive member 138, and the second jaw member 126 attached thereto, relative to the elongate shaft member 110. In some embodiments, the drive member 138 may be spring loaded with respect to the trigger 120 such that the second jaw member 126 is biased toward a resting, extended position. Because the second jaw member 126 is aligned with the channel 122 of the elongate shaft member 110, the second jaw member 126 may be positioned to translate partially or entirely within the channel 122 of the elongate shaft member 110. The drive member 138 and the second jaw member 126 may be attached in any suitably secured manner, e.g., adhered, welded, brazed, press fit, interference fit, snap fit, etc.

The second jaw 126 has a similar configuration to the first jaw member 124 described above. In particular, the second jaw member 126 has a substantially tapered profile along the longitudinal axis X to define a distal surface 140 that is configured to make an initial contact with tissue, e.g., to press, move, or dilate tissue. The second jaw member 126 also defines a tissue contacting surface 142. The tissue contacting surface 142 may have a substantially flat profile, as shown, and includes a plurality of ultrasound transducers 144 thereon. The ultrasound transducers 144 may be arranged in any suitable manner, e.g., longitudinally spaced rows, as described above with respect to the first jaw member 124. Accordingly, the ultrasound transducers 144 of the second jaw member 126 may be electrically coupled with ultrasound generator 103 (FIG. 1) via wires 136 to transmit ultrasonic energy therethrough.

Additionally, the second jaw member 126 may include a light source 146 disposed thereon. (See FIG. 2A) The light source 146 may be disposed in substantially planar relation with the tissue contacting surface 142, as shown. The light source 146 is configured to transmit light, e.g., a laser beam, from the tissue contacting surface 142 of the second jaw member 126 toward tissue. The light source 146 may be configured to transmit any type or configuration of light therefrom, e.g., visible, ultraviolet or infrared. Additionally, the light source 146 may have any desirable configuration for its intended purpose, e.g., a light emitting diode or laser diode.

It will be understood that the components of the ultrasound device 102 may have any desirable configuration or arrangement. The components of the ultrasound device 102 may be formed of any suitable materials for their respective purposes, e.g., biocompatible polymers, metals, or composites. It will further be understood that while the ultrasound device 102 has been described with respect to use in minimally invasive procedures, the ultrasound device 102 is suitable for use in traditional open-type surgical procedures.

The first jaw member 124 is configured to pivot at the hinge 128 to move from a first, open position, to a second, approximated position. Accordingly, the end effector 112 is configured to close about and capture, e.g., a section of tissue "T". (See FIG. 3B.) The first jaw member 124 may exert a compressive force on tissue T against the second jaw member 126 such that tissue T is compressed therebetween.

In embodiments, the first jaw member 124 may be configured to exert a variable or user-defined compressive force on tissue T.

Once tissue T is appropriately disposed between the jaw members 124, 126, the ultrasonic transducers 134 and 144 are activated and acoustic energy "A" is applied to the tissue T. An electrical signal may be transmitted to ultrasound transducers 134 and 144, e.g., from ultrasound generator 103 (FIG. 1) via wires 136, which convert the electrical signal into acoustic energy.

As acoustic energy A is transmitted through tissue T, reflected energy "E" is reflected off tissue structures, e.g., tissue surface T. Because ultrasound transducers 134 and 144 are located on either side of the tissue T, i.e., ultrasonic transducers 134 and 144 are disposed on both the first and second jaw members 124, 126, acoustic energy may be applied about either side of a target region of tissue, i.e., node N. Accordingly, a node N that is disposed deep within tissue T such that ultrasound imaging procedures may be obscured by e.g., particularly dense regions of tissue T, can be completed more effectively via the application of acoustic energy A to either side of tissue T containing node N. Additionally, the ultrasonic transducers 134 and 144 disposed on one of the first and second jaw members 124, 126 may be configured to transmit acoustic energy A to the ultrasonic transducers 134 and 144 disposed on the other of the first and second jaw members 124, 126, which may be configured to receive reflected energy E such that acoustic energy A passes from one side of the tissue T to another. In this manner, additional properties of tissue T, e.g., thickness or the rate of fluids flowing therethrough, may be measured.

The ultrasound transducers 134 and 144, as described above, are configured to receive the reflected energy E and produce an electrical signal based on the reflected energy E. Accordingly, as the reflected energy E received from different portions of the tissue T has different properties due to the acoustic impedance of different portions of tissue T, ultrasonic transducers 134 and 144 produce different electrical signals in response to the reflected energy E received from those portions of tissue T.

Figure 4:
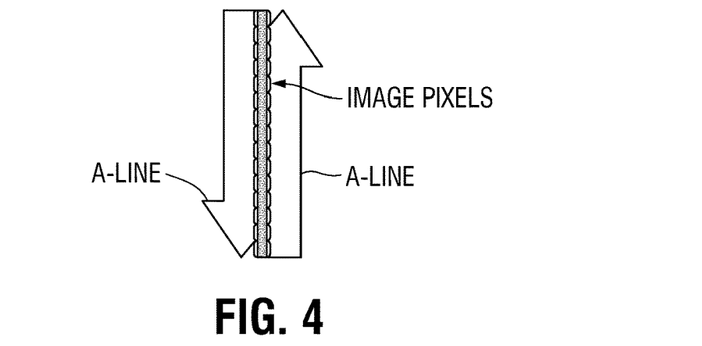
FIG. 4 is a graphical representation of image pixels obtained using the imaging techniques described.

With additional reference to FIG. 1, and as shown in FIG. 4, ultrasound device 102 may be electrically coupled with the controller 104, which is configured to interpret the electrical signals received from ultrasonic transducers 134 and 144. The controller 104 converts the electrical signals from the ultrasound transducers 134, 144 into A-lines. In ultrasound imaging, "A-lines" are horizontal, regularly spaced hyperechogenic lines representing reverberations of the pleural line. The controller 104 averages the opposing A-lines to generate an average A-line. The average A-line is used by the controller 104 to generate image pixels that form the ultrasound image. The controller 104 then provides a signal to the display 106 for displaying the generated image, e.g., 2D- or 3D-visual or graphical representations of data collected by the ultrasound transducers 134 and 144. In this manner, the controller 104 provides an interface, externally of a patient, that enables an operator to visualize sub-surface tissue structures.

The controller 104 may include an input device (not shown) to permit a clinician to control the imaging procedure. A processor (not shown) within the controller 104 receives the input from the input device and the ultrasound transducers 134, 144 to generate the image provided to the display 1-6. The controller 104 is controlled by software that may be stored on a memory (not shown).

Figure 5:
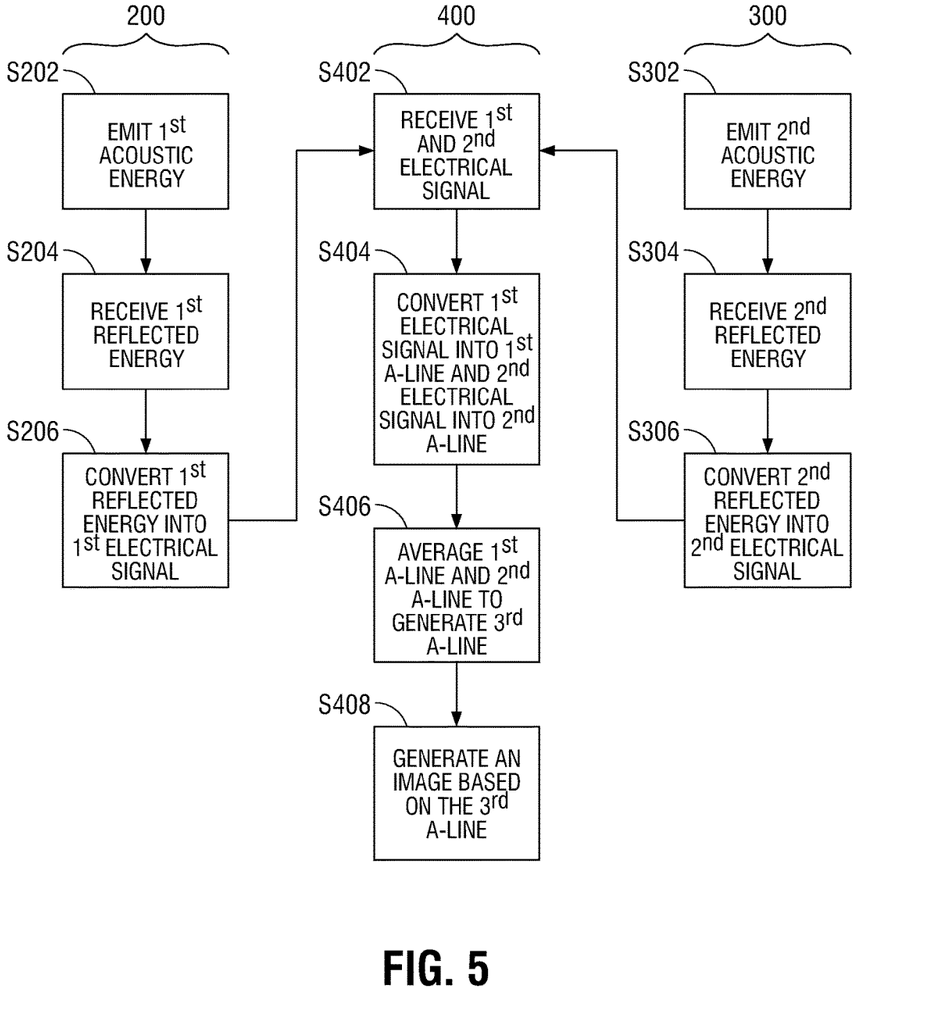
FIG. 5 herein is a flowchart depicting a speckle reduction method in according to the present disclosure.

The ultrasound imaging system of the present disclosure is used to reduce speckle noise that may appear in ultrasound images. FIG. 5, which will be discussed in conjunction with FIGS. 1-3B, depicts a method to reduce speckle in an ultrasound image. As shown in FIG. 5, the method involves a process 200 for generating a first signal, a process 300 for generating a second signal, and a process 400 for generating an image. Processes 200, 300, and 400 may be executed by a processor (not shown) in the controller 104. Further, processes 200 and 300 may be executed sequentially or simultaneously.

As shown in step s202 of FIG. 5, the ultrasound transducer 134 emits a first acoustic energy toward tissue T while in step s302, the ultrasound transducer 144 emits a second acoustic energy toward tissue T. The ultrasound transducer 134 receives a first reflected energy based on the first acoustic energy in step s204 and the ultrasound transducer 144 receives a second reflected energy based on the second acoustic energy in step s304. In some embodiments, the ultrasound transducer 134 may receive a first reflected energy based on the second acoustic energy and the ultrasound transducer 144 may receive a second reflected energy based on the first acoustic energy. In step s206, the first reflected energy is converted into first electrical signal and in step s306, the second reflected energy is converted into a second electrical signal by the ultrasound transducers 134 and 144, respectively.

The first and second electrical signals are received by the controller 104 in step s402. In step s404, the first electrical signal is converted into a first A-line and the second electrical signal is converted into a second A-line. The first A-line and the second A-line are averaged to generate a third A-line in step s406. In step s408, the third A-line is used to generate the image.

It will be understood that various modifications may be made to the embodiments disclosed herein. For instance, the end effector 112 may be disposed at a distal end of a catheter (not shown) for surgical procedures performed intravascularly. Therefore, the above description should not be construed as limiting, but merely as exemplifications of preferred embodiments. Those skilled in the art will envision other modifications within the scope and spirit of the claims.

The invention claimed is:

1. An ultrasound imaging system comprising:
   an ultrasound device including:
      a handle assembly;
      an elongate shaft member extending from the handle assembly;
      an end effector coupled to a distal end of the elongate shaft member, the end effector having a first jaw member and a second jaw member opposite the first jaw member, the first jaw member and the second jaw member move relative to one another to grasp tissue therebetween;
      a first ultrasound transducer disposed on the first jaw member; and
      a second ultrasound transducer disposed on the second jaw member; and
   a controller configured to receive a first signal from the first ultrasound transducer and a second signal from the second ultrasound transducer, the controller generates an image based on the first signal and the second signal.

2. The ultrasound imaging system of claim 1, wherein the first ultrasound transducer includes a linear array of ultrasound transducers.

3. The ultrasound imaging system of claim 1, wherein the second ultrasound transducer includes a linear array of ultrasound transducers.

4. The ultrasound imaging system of claim 1, wherein the first ultrasound transducer emits a first acoustic energy and receives a first reflected energy based on the first acoustic energy, the first ultrasound transducer converts the first reflected energy into the first signal.

5. The ultrasound imaging system of claim 4, wherein the second ultrasound transducer emits a second acoustic energy and receives a second reflected energy based on the second acoustic energy, the second ultrasound transducer converts the second reflected energy into the second signal.

6. The ultrasound imaging system of claim 5, wherein the controller converts the first signal into a first A-line and the second signal into a second A-line.

7. The ultrasound imaging system of claim 6, wherein the first A-line and the second A-line are averaged to produce a third A-line.

8. The ultrasound imaging system of claim 7, wherein the controller generates the image from the third A-line.

9. The ultrasound imaging system of claim 1, wherein the first ultrasound transducer emits a first acoustic energy and the second ultrasound transducer emits a second acoustic energy.

10. The ultrasound imaging system of claim 9, wherein the first ultrasound transducer:
receives a first reflected energy based on the second acoustic energy; and
converts the first reflected energy into the first signal; and
wherein the second ultrasound transducer:
receives a second reflected energy based on the first acoustic energy; and
converts the second reflected energy into the second signal.

11. The ultrasound imaging system of claim 10, wherein the controller converts the first signal into a first A-line and the second signal into a second A-line.

12. The ultrasound imaging system of claim 11, wherein the first A-line and the second A-line are averaged to produce a third A-line.

13. The ultrasound imaging system of claim 12, wherein the controller generates the image from the third A-line.

14. A method for reducing speckle in an ultrasound image provided by an ultrasound imaging system, the ultrasound imaging system having a controller and an ultrasound device that includes an end effector having a first ultrasound transducer disposed on a first jaw member opposite a second ultrasound transducer disposed on a second jaw member, the method comprising:
grasping tissue between the first and second jaw members;
emitting a first acoustic energy from the first ultrasound transducer;
emitting a second acoustic energy from the second ultrasound transducer;
receiving a first reflected energy based on the first acoustic energy at the first ultrasound transducer;
receiving a second reflected energy based on the second acoustic energy at the second ultrasound transducer; and
generating an image based on the first reflected energy and the second reflected energy.

15. The method according to claim 14, including:
converting the first reflected energy into a first signal that is provided to the controller; and
converting the second reflected energy into a second signal that is provided to the controller.

16. The method according to claim 15, wherein generating the image includes:
converting the first signal into a first A-line;
converting the second signal into a second A-line;
averaging the first A-line and the second A-line to generate a third A-line;
generating the image based on the third A-line.

17. A method for reducing speckle in an ultrasound image provided by an ultrasound imaging system, the ultrasound imaging system having a controller and an ultrasound device that includes an end effector having a first ultrasound transducer disposed on a first jaw member opposite a second ultrasound transducer disposed on a second jaw member, the method comprising:
grasping tissue between the first and second jaw members;
emitting a first acoustic energy from the first ultrasound transducer;
emitting a second acoustic energy from the second ultrasound transducer;
receiving a first reflected energy based on the second acoustic energy at the first ultrasound transducer;
receiving a second reflected energy based on the first acoustic energy at the second ultrasound transducer; and
generating an image based on the first reflected energy and the second reflected energy.

18. The method according to claim 17, including:
converting the first reflected energy into a first signal that is provided to the controller; and
converting the second reflected energy into a second signal that is provided to the controller.

19. The method according to claim 18, wherein generating the image includes:
converting the first signal into a first A-line;
converting the second signal into a second A-line;
averaging the first A-line and the second A-line to generate a third A-line;
generating the image based on the third A-line.

* * * * *